US008814936B2

(12) United States Patent
Draenert

(10) Patent No.: US 8,814,936 B2
(45) Date of Patent: Aug. 26, 2014

(54) POROUS MATERIAL FOR USE AS IMPLANT, BONE REPLACEMENT AND IN GENERAL AS MATERIAL

(75) Inventor: Klaus Draenert, Munich (DE)

(73) Assignee: Boneartis AG, Brunnen (CH)

(*) Notice: Subject to any disclaimer, the term of this patent is extended or adjusted under 35 U.S.C. 154(b) by 1040 days.

(21) Appl. No.: 11/570,205

(22) PCT Filed: Jun. 7, 2005

(86) PCT No.: PCT/EP2005/006115
§ 371 (c)(1),
(2), (4) Date: Dec. 14, 2006

(87) PCT Pub. No.: WO2005/120399
PCT Pub. Date: Dec. 22, 2005

(65) Prior Publication Data
US 2008/0319547 A1   Dec. 25, 2008

(30) Foreign Application Priority Data
Jul. 6, 2004   (DE) .......................... 10 2004 027 657

(51) Int. Cl.
*A61F 2/28* (2006.01)
(52) U.S. Cl.
USPC ..................................................... 623/16.11
(58) Field of Classification Search
USPC ..................................................... 623/16.11
See application file for complete search history.

(56) References Cited

U.S. PATENT DOCUMENTS

| 3,899,556 A | * | 8/1975 | Heide et al. ...................... 264/44 |
| 4,906,423 A | * | 3/1990 | Frisch .............................. 264/48 |
| 5,167,271 A | * | 12/1992 | Lange et al. ................... 164/103 |

(Continued)

FOREIGN PATENT DOCUMENTS

| DE | 2242867 | 5/1974 |
| DE | 3903695 | 8/1990 |

(Continued)

OTHER PUBLICATIONS

Irwin RB, Bernhard M, Biddinger A (2001) Coralline hydroxyapatite as bone substitute in orthopaedic oncology. Am J Orthop 30:544-550 (Abstract only).

(Continued)

*Primary Examiner* — Randy Shay
(74) *Attorney, Agent, or Firm* — Peter J. Ims; Westman, Champlin & Koehler, P.A.

(57) ABSTRACT

Implants and methods for producing same are described, the implants featuring an adjustable porous shell, the inside being continuously interconnectingly adjustably porous and which can be sintered net shaped; these implants exhibit a high compression stability and show, when being combined with filler materials with or without active agents, different chemical, physical-mechanical, biomechanical or also pharmacological properties. The essential features of the manufacturing process are described in FIG. (1) and comprise expandable shaping elements, deformable elastic tools, the application of defined negative pressures, temperatures during defined application periods in combination with combined materials, which can be separated from each other physically, chemically or mechanically and removed.

31 Claims, 4 Drawing Sheets

(56) References Cited

U.S. PATENT DOCUMENTS

| | | | |
|---|---|---|---|
| 5,549,123 A * | 8/1996 | Okuyama et al. | 128/898 |
| 5,677,355 A * | 10/1997 | Shalaby et al. | 521/61 |
| 5,969,020 A * | 10/1999 | Shalaby et al. | 524/167 |
| 6,248,130 B1 * | 6/2001 | Perry | 623/6.64 |
| 6,316,091 B1 * | 11/2001 | Richart et al. | 428/310.5 |
| 6,471,993 B1 * | 10/2002 | Shastri et al. | 424/486 |
| 6,479,418 B2 * | 11/2002 | Li et al. | 501/81 |
| 7,449,236 B2 * | 11/2008 | Lanphere et al. | 428/402 |
| 7,875,342 B2 * | 1/2011 | Smith et al. | 428/312.2 |
| 2003/0039676 A1 | 2/2003 | Boyce et al. | |
| 2003/0236573 A1 | 12/2003 | Evans et al. | |
| 2005/0043585 A1 * | 2/2005 | Datta et al. | 600/153 |
| 2006/0198939 A1 * | 9/2006 | Smith et al. | 427/2.1 |

FOREIGN PATENT DOCUMENTS

| | | |
|---|---|---|
| DE | 10248056 A1 | 4/2004 |
| EP | 0204786 | 12/1986 |
| EP | 0553167 | 8/1993 |
| EP | 0605799 A1 | 12/1993 |
| WO | 9206653 A1 | 4/1992 |
| WO | 95/21053 | 8/1995 |

OTHER PUBLICATIONS

Written Opinion (including translation) for International (PCT) Patent Application No. PCT/EP2005/006115.

International Preliminary Report on Patentability (including translation) for International (PCT) Patent Application No. PCT/EP2005/006115, mailed Dec. 28, 2006.

International Search Rep0ort dated Oct. 13, 2005, for PCT Application No. PCT/EP2005/006115.

European Search Report and Written Opinion including English Translation of Written Opinion dated May 2, 2014 for corresponding European Patent Application No. 11187799.9, 11 pages.

European Search Report and Written Opinion including English Translation of Written Opinion dated May 6, 2014 for corresponding European Patent Application No. 11187802.1, 8 pages.

European Search Report and Written Opinion including English Translation of Written Opinion dated May 6, 2014 for corresponding European Patent Application No. 11187800.5, 11 pages.

European Search Report and Written Opinion including English Translation of Written Opinion dated May 2, 2014 for corresponding European Patent Application No. 11187798.1, 9 pages.

* cited by examiner

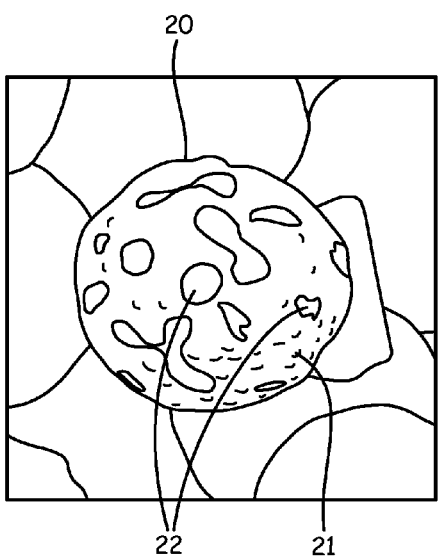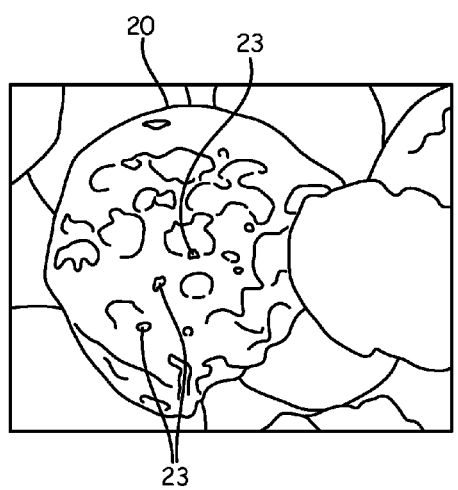
FIG. 2a
FIG. 2b

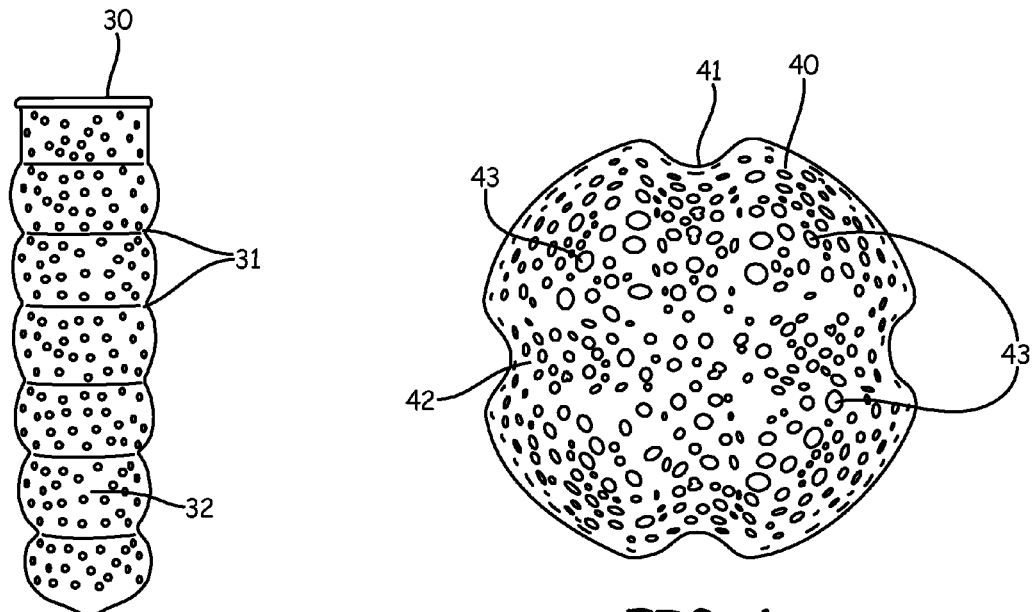
FIG. 3
FIG. 4
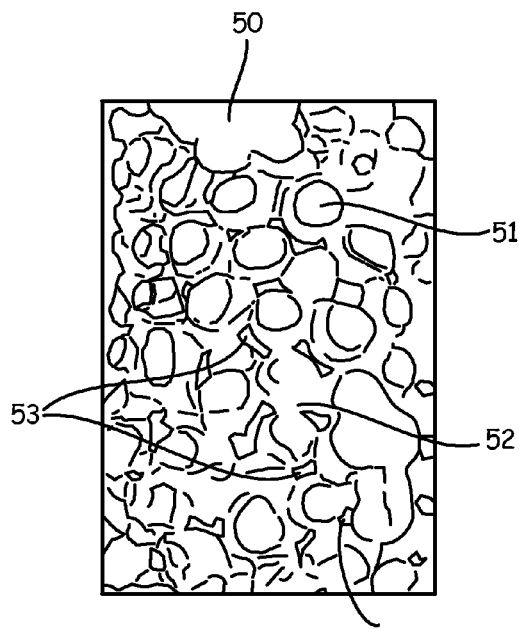
FIG. 5

POROUS MATERIAL FOR USE AS IMPLANT, BONE REPLACEMENT AND IN GENERAL AS MATERIAL

CROSS REFERENCE TO RELATED APPLICATION

This application is a national stage application under 35 U.S.C. 371 of PCT Application No. PCT/EP2005/006115 having an international filing date of Jun. 7, 2005, which designated the United States, which PCT application claimed the benefit of German Application Serial No. 102004027657.9, filed Jun. 7, 2004, the entire disclosure of which is hereby incorporated herein by reference.

BACKGROUND OF THE INVENTION

In surgery of the skeletal system, there has always been a need to re-fill bone defects after fractures, the removal of tumors, a loss of bone substance after inflammations or in connection with bone cysts, with bone material or a substitute material similar to bone. For this purpose, partial bovine substitute material was used. An alternative possibility for therapy for bone defects includes material of coral reefs processed in laboratories (replaminiform processes) and inserted. Both materials have the drawback that they are biological materials and have structures, which can no longer be influenced and which are hard to produce in a standardized manner. Both materials incorporate anisotropy in structure and properties of a grown biological structure and are, in most cases, too stiff. A method for manufacturing such biological substitute materials is described in DE-A-3903695. Synthetic substitute materials can be manufactured from pure raw materials. However, they lack a regular structure that is similar to the bone. Such a synthetic material is foamed Ceros® artificial bone materials; said materials lack the ability for bone to grow through them, since the pores are mostly closed.

In U.S. Pat. No. 3,899,556, a method comprising a preformed shaping frame is described, featuring a dense filling of balls, in which the shaping elements are poured with a solvent and are glued together in this way. However, with such a method, no regular, porous, interconnecting material can be produced in a standardized way because the regions of adherence or gluing together were too irregular and the solvent process or action was not sufficiently controllable. In EP 0553167 and EP 0204786, the problem was partially solved, in that deformable shaping elements were pressed on each other in contact by applying pressure, and were in this state surrounded by a frame-forming mass, which was subsequently cured and freed from the shaping elements either chemically or thermally. The implants produced in this way showed beautiful and nearly regular interconnections in that half of the implant which faced the applied pressure. However, in the other half of the implant not facing the pressure, numerous closed pores were formed. The reason is that deformable and only partially elastic shaping elements dampen the applied force, and the deforming effect is weakened by the dampening, such that no regular and continuous interconnection of the material can be achieved. Surprisingly, a method was now found which avoids said phenomena and achieves a completely regular deformation of all shaping elements associated with this process. Said method is economic and completely reproducible.

BRIEF SUMMARY OF THE INVENTION

An implant body of the present invention comprises a porous implant body including an outer shell having a surface, penetrated by pores having an adjustable diameter, and an inner structure, comprising a conglomerate of cavities surrounded by sphere-shaped shells. The cavities form a connected cavity system made of hollow sphere-shaped cavities, which cavity system is continuously interconnected. The cavities of said cavity system have an adjustable diameter. A shell framing encompasses said cavity system. The implant body is configured such that a pore of the outer shell has a diameter smaller than a diameter of a cavity of the cavity system connected therewith.

The implant body may be shaped as a cylinder and may be configured such that the outer shell is structured in the shape of helical crossings formed of at least one of contractions and bulges.

The implant body may be configured such that the inner structure corresponds to a bowl-shaped sponge bone or cancellous bone.

The diameter of the pore of the outer shell is smaller than the diameter of the cavity connected therewith, in ratios of between 1:5 to 1:1.5, and more particularly with the preferred range of ratios of 1:2 to 1:3.

The implant body may be configured such that the frame material is selected from a group consisting of a calcium phosphate, a hydroxyapatite, a calcium carbonate, a calcium-sulfate-composition, an aluminum oxide ceramic, a collagen, a polyaminoacid, an absorbable polymer, an acrylate or derivate thereof, a polymethyl-methacrylate, and a metal preferably a cobalt-chromium-molybdenum (CoCrMo) alloy, titanium, tantalum and alloys thereof.

The implant body may be configured such that the cavity system is optionally coated with a filler material having dampening or reinforcing properties, in a manner that the filling is restricted to the inside of the implant body and selectively completely fills same. The filler material may be an absorbable or non-absorbable organic or inorganic filler material.

The implant may further be configured such that the filler material is selected from a group consisting of a poly-amino acid, a polylactide, polyglactine, glycoside, polyacetals, poly-acid amides and polyester.

The implant body may be configured such that at least some individual cavities are filled with a material comprising an active agent which is released and centrifugally distributes by diffusion over the implant surface.

The implant body may be configured such that said implant body includes at least one of an active agent, consisting of a growth factor, a bone morphogenetic protein or combination thereof, an antibiotic, a hormone, an immunosuppressive drug, a cytostatic, and an antibiotic including combinations thereof. The antibiotic may comprise one of Gentamycin, Clindamycin, Streptomycin and other bacteriostatic and bactericide agents.

The implant body may be configured such that wide and narrow cavity systems are formed therein, and that the cavities permit filling selectively with filler materials and agents or combinations thereof.

The implant body may be configured such that cavities of different sizes are structured with an interconnected framing including a large cavity having a shell-shaped wall made of hydroxyapatite and having a shell-shaped structured framing made of an easily absorbable tri-calciumphosphate, wherein a continuously combined implant body, comprising hydroxyapatite and tri-calciumphosphate, is generated.

The implant body may have differing porosity, and may selectively include at least one of a filler material and an active agent in its cavity system.

An implant device may comprise a first implant body and a second implant body mechanically inserted in said first implant body, and said implant device may be composed of one of a porous and solid material and may selectively have an active agent that is one of absorbable and non-absorbable.

BRIEF DESCRIPTION OF THE DRAWINGS

FIGS. 2a and 2b show ceramic implants of the invention;

FIG. 3 is an implant of the invention in the form of a bone dowel;

FIG. 4 is an eye implant of the invention; and

FIG. 5 is an implant of the invention in the form of a sphere conglomerate.

DETAILED DESCRIPTION OF THE INVENTION

Figure 1:
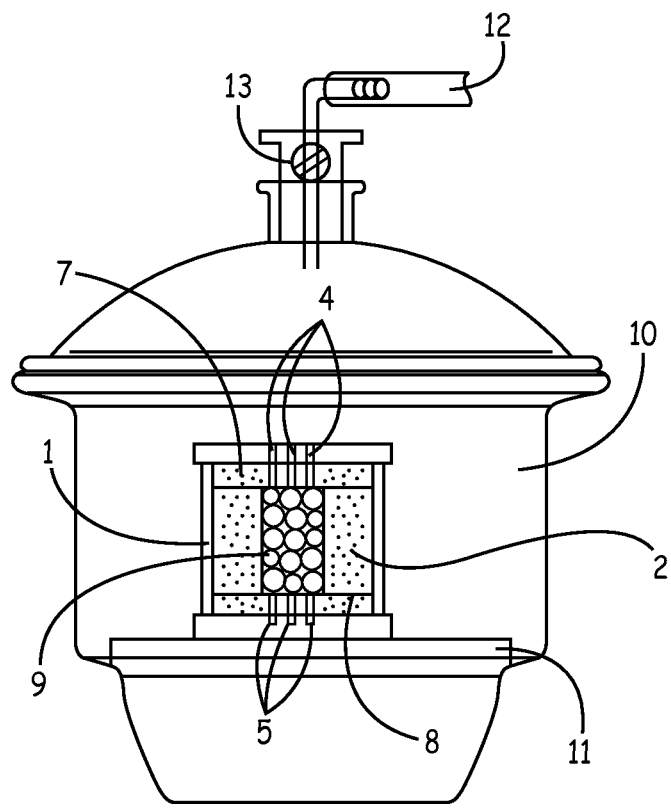
FIG. 1 is a vacuum chamber for use in producing an implant of the invention.

The use of a negative pressure applied on the shaping elements in a method for producing a bone implant surprisingly led to a desired result. The shaping elements are filled loosely into a tool and are charged with or subjected to a defined negative pressure in a vacuum-sealed system and subsequently the frame-forming mass is added to the tool utilizing the suction and cured by applying the defined negative pressure to the shaping elements and frame forming mass at a defined temperature over a defined period of time. Alternatively, the shaping elements are charged with or subjected to the defined negative pressure together with the frame forming material after the filling of the tool with the frame forming material and simultaneously cooled-down, e.g. by a metal setting plate of the tool.

This arrangement led to further standardized results and comprises the following steps: the loose filling of shaping elements into the tool and the structure-forming framing material mass was added, and the closed tool or container, which was not vacuum-sealed, was subjected to a defined negative pressure at a defined temperature and over a defined period of time under vacuum, and the material and tool were simultaneously cooled-down through the setting or cooling plate of the tool. The simple handling of this process made the result highly reproducible.

However, also this result could surprisingly be further enhanced in view of the adjustable porosity of the surface by utilizing a deformable silicone mould instead of a solid metallic tool. This resulted in the implant, dependent on the applied negative pressure, having a continuous porosity extending up to the surface, said porosity being controllable through the amount of negative pressure on the one side and the elastic modulus of the tool on the other side. This method enables one to achieve a continuous porosity even if the shaping elements were not expandable, e.g. not air-containing, but were e.g. sugar spheres.

As the shaping elements in this method, preferably expandable polystyrene spheres (EPS) are used, e.g. Styrofoam® F414 expanded polystyrene, which is foamed with pentane as an expanding agent. Upon applying a negative pressure, these spheres expand very fast and increase in volume. In this way, the contact bridge between the spheres becomes wider and therewith determines the diameter of the interconnecting passages in the frame-forming material up to the surface. Upon using of a silicone tool, the spheres squeeze into the silicone wall and, furthermore, the negative pressure draws the deformable wall over the sphere surfaces into the implant.

Foamed materials to be used as shaping elements are preferably employed, also those to which an expanding agent was added, which is activated at a specific temperature or under specific preconditions. An especially preferred material is Styrofoam® F414 expanded polystyrene, having a preferred volumetric weight of the foamed polystyrene between 17 g/l and 70 g/l, preferably approx. 20 g/l to 35 g/l. The grain size distribution of the foamed material lies between 200 µm and 15 mm, and one can also use sizes between 1000 µm and 3000 µm. In order to determine the expansion and the deformability of the individual shaping elements, experiments were performed to determine the parameters in a simple manner, said parameters being required for the standardization of the method. For this purpose, different shaping elements having different volumetric weights, e.g. differently foamed polystyrene spheres having different diameters, were filled into a cylinder with movable, vacuum-sealed abutting pistons up to a defined height of 84.3 mm and exposed to a defined vacuum. From the change of the original height in dependency of the applied negative pressure, quantities were determined which represent an initial reduction of volume by removal of air between the shaping elements, followed by an expansion of volume which was adjustable to the former initial length by applying a force F, measured in N, and which represented the expansion pressure of the air in the shaping elements. Depending on the time period, the force slowly decreased, which could be explained by the bursting of the air bubbles in the plastics. Based on this phenomenon, the defined time periods for the charging with negative pressure were determined.

Pressures between 150 mbar and 800 mbar, preferably approximately 300 mbar to 500 mbar, over a time period of 15 minutes, applied on a phosphate-agar mixture, at a temperature of the implant of 4 to 12° C., showed especially advantageous results in view of the outside porosity and the inner interconnections.

Deformable moulds, in particular silicones having a Shore hardness below 25 Shore, preferably below 18-20 Shore, that can be used in casting or injection die casting methods are suitable. However, all plastically or elastically deformable materials can be used, the elastic modulus of which lies clearly below that of the shaping elements. Correspondingly, the tools can be cast, but also can be manufactured in mass production with injection moulding methods. Examples for plastically deformable tools are tools made of Styrofoam® expanded polystyrene having different density, examples for elastically deformable tools are the aforementioned silicones, wherein foamed silicones can also be used. These materials expand under negative pressure, and the expansion pressure of said materials in vacuum adds to the above described effect of the expandable shaping elements.

Castable framing materials including a mixture of hydroxylapatite (HA) or tricalciumphosphate (TCP) and an agar solution in a ratio of 10 g powder/7 ml to 25 ml solution, which corresponds to a ratio of 1.4 to 0.4, are preferably used. Ideal preparations include a mixing ratio powder/solution that corresponds to 0.45 to 0.48, e.g. 1600 g HA for 3500 ml of solution.

Depending on the composition, the shrinking factor can already be calculated on the basis of the preparation and lies between 0.95 to 2.9, preferably between 1.75 and 2.15. For a HA-agar mixture capable of flowing, which is filled at a temperature of 60° C., at a ratio of 16 g/35 ml of a 1.7% agar solution, the shrinking factor is exactly 1.91. Upon these preconditions, i.e., expandable shaping elements, a deformable silicone mould and an exact preparation with defined shrinking, very precise implants could be sintered net shaped, without the necessity of a post-processing.

The definite design multiplied with the shrinking factor leads, e.g., to an implant body made of plastics or any other material being easily processable in a CAD/CAM process, which is re-cast with a castable silicone in an original mould up to the top edge. After curing of the silicone, the shaping body can be easily mechanically removed. The silicone mould is perforated several times at the bottom and is subsequently filled with polystyrene spheres of a desired size, then closed with a silicone lid having venting holes. The mould or tool is then filled with a ceramic material forming a ceramic mass. Immediately after the filling, the tool or mould is subjected to a negative pressure in a vacuum and drying chamber and cooled down to 4-12° C., e.g., through a setting or cooling plate. After curing of the ceramic mass, the tool can be de-assembled and the body of ceramic material and expanded polystyrene spheres can be easily removed. In an acetone washing, the spheres of Styrofoam® expanded polystyrene are dissolved from the ceramic mass, which forms the implant body. The ceramic mass forming the implant body is dehydrated in a series of steps using 70/80/90 and 100% acetone, respectively. After each wash step the implant body is dried in air while it cools (cool drying). The weight of the implant body is documented every hour by means of a precision scale; if no further loss of weight in the air begins to show and the curve of the weight remains linearly unchanged, the implant body is dried for 24 hours in a vacuum and drying chamber by adding $P_2O_5$ in a vacuum of 150-250 mbar absolute pressure. The implant body is subsequently sintered at 1300° C. in a sintering furnace. This results in an open pore implant body that is true to size, and which has a clearly higher strength compared to mechanically post-processed bone substitute material cylinders or cubes. Said strength of the implant body can be further increased by an outside structuring, e.g. rings, contractions, massive edges etc.

In FIG. 1, a simple vacuum and drying chamber (10) is described, comprising a venting valve (13) and a tap for attaching a pipe leading to the vacuum pump (12) and a metallic cooling plate (11) having a filling tool (1) arranged on the cooling plate (11) and having a deformable tool received in a flush manner. The deformable tool comprises three parts, a body (2) that contains spherical shaping elements (9), a lid (7) with perforations (4) and a bottom (8) with perforations (5) for filling of a material such as a ceramic mass into the deformable tool.

In FIGS. 2*a* and 2*b*, ceramic implants (20) according to the invention are shown, in FIG. 2*a* in a plan view and in FIG. 2*b* as a sectional view upon breaking open. The plan view of the sphere shell shows the open pores (22) and the rough shell (21). In the sectional view, the interconnecting pore structure (23) is shown.

In FIG. 3, an implant according to the invention is shown as a bone dowel (30), e.g. for re-fixing a ligament in case of a cruciate ligament substitute across the outside of the dowel. The dowel (30) comprises horizontal (31) contractions, which can preferably also be arranged helically, and the outer shell is interrupted by spaced pores (32) across the complete surface.

In FIG. 4, a light ceramic implant (40) is shown, sintered in this shape, having open pores across the complete outer surface (43), and comprising crossing depressions or channels (41, 42), in which the eye muscles can be sewed, and which is used as a part of an artificial eye.

FIG. 5 shows a sphere conglomerate (50) consisting of solid spheres or sphere elements (51), which may however also consist of the elements of FIG. 2. The sphere conglomerate (50) features wide bridges (52) between the sphere elements and regular sphere intervals (53) that form pores or cavities.

Figure 6:
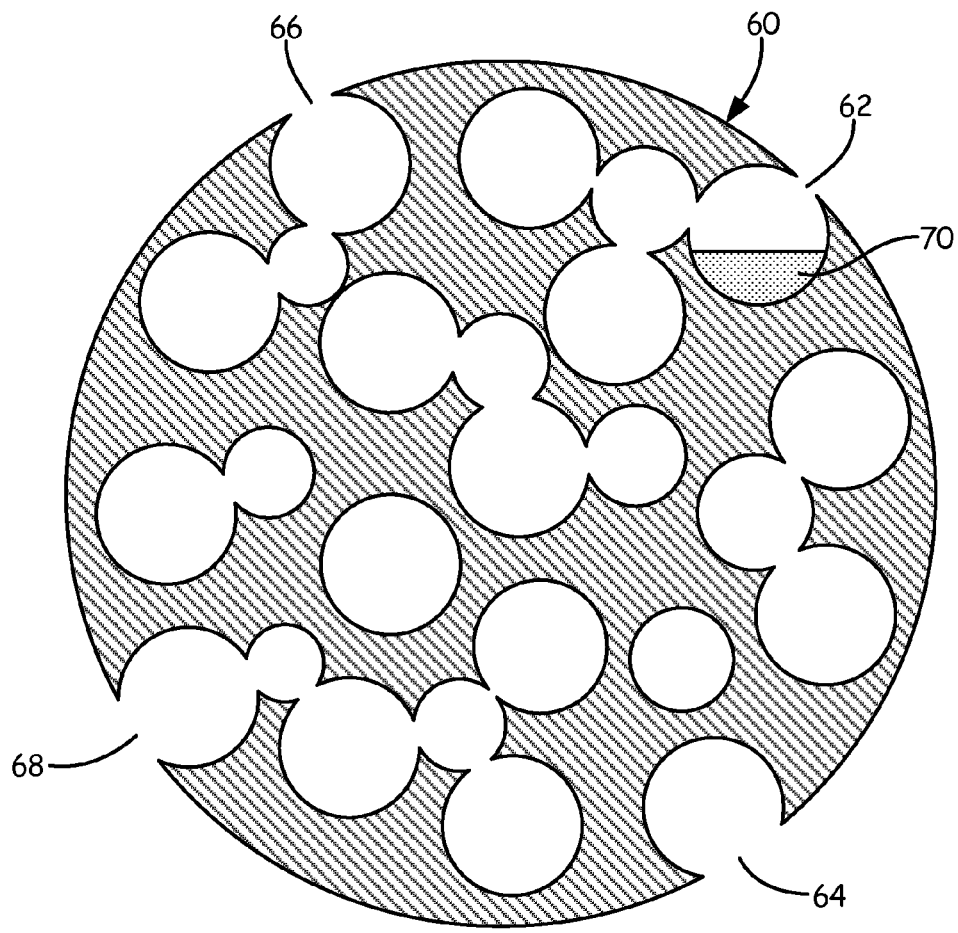
FIG. 6 is a sectional view of a spherical ceramic implant having a range of ratios of pore size to maximum diameter of the directly connected cavity along with a filler material in a cavity.

In FIG. 6 a cross-section of a porous implant 60 is illustrated. The diameter of the pore of the outer shell is smaller than the diameter of the cavity connected therewith, in ratios of between 1:5 as illustrated at 62 to 1:1.5 as illustrated at 64, and more particularly with the preferred range of ratios of 1:2 as illustrated at 66 to 1:3 as illustrated at 68.

The implant body 60 may be configured such that the cavity system is optionally coated with a filler material 70 having dampening or reinforcing properties, in a manner that the filling is restricted to the inside of the implant body and selectively completely fills same. The filler material 70 may be an absorbable or non-absorbable organic or inorganic filler material.

EXAMPLES

Example (1)

Styrofoam® expanded polystyrene spheres having a diameter of 12 mm are immersed and introduced into a forming tool that is filled with hot wax having a temperature of 90° C. and being taken from the heating furnace for this purpose, said forming tool being within a cylindrical container having a perforated bottom with boreholes of 10-11 mm in diameter and a fixable lid seated flush on the spheres and having the same size boreholes. The forming tool with the wax and Styrofoam® expanded polystyrene spheres, fits flush into a cylindrical mould which has a removable bottom. After curing of the wax at room temperature, the bottom of the cylindrical mould is removed and the forming tool containing the wax and Styrofoam® expanded polystyrene spheres is pressed out. The forming tool holding the wax and Styrofoam® expanded polystyrene spheres is also separated from its bottom and lid and the formed wax-Styrofoam® expanded polystyrene spheres cylinder is pressed out and the Styrofoam® expanded polystyrene spheres are removed in an acetone washing. After drying in air, the resulting continuous, interconnecting, porous wax framing is inserted into a filling container receiving the framing in a flush manner.

The filling container has a filler neck with perforations at the bottom of the container and may also contain a screen which is required for suctioning smaller Styrofoam® expanded polystyrene spheres into the cavity system of the wax framing. Furthermore, the filling container is provided with a lid having venting boreholes, e.g., having a diameter of 1.5 to 2.5 mm. Styrofoam® expanded polystyrene spheres having a diameter of e.g. 600-1200 μm are suctioned into the cavities in the wax framing, wherein a screen having a mesh size of 400 μm is arranged upstream. The cavity system of the wax framing is completely filled with the smaller Styrofoam® expanded polystyrene spheres and is then closed with a lid.

The filling container is now filled with a ceramic mass, wherein the ceramic material forming the ceramic mass is filled into the filling container through the filler neck and suctioned in through the venting holes or the ceramic material is filled into the filling container without pressure simply through the filler neck. If the ceramic mass protrudes through the venting holes of the lid, the mould is filled and is put into a vacuum and drying chamber together with the tool and charged with a negative pressure of 500-600 mbar for 15 minutes and cooled-down during this time period by the metallic setting or cooling plate shown at (11) in FIG. 1.

The thus cured wax-ceramic-Styrofoam® expanded polystyrene spheres are subsequently washed in acetone to remove the Styrofoam® expanded polystyrene in the acetone washing, dried in air and sintered together with the wax in a furnace at 1300° C. This results in completely isolated, at the outside a continuously porous and at the inside interconnected porous spheres having a diameter of 6 mm. Due to the shrinking of the matrix material, completely separated spheres are formed.

Example (2)

Instead of individual porous spheres, an interesting material may be produced, which corresponds to a negative print of the marrow combs, and a sphere conglomerate having gaps between the porous spheres for the ingrowing of bone trabeculae and wide connecting bridges, which correspond to the contact points of the spheres: The steps correspond to example 1, however, the wax-Styrofoam® expanded polystyrene framing or body is exposed to a defined negative pressure of e.g. 600 mbar during the curing in the vacuum and drying chamber. The following expansion of the Styrofoam® expanded polystyrene spheres results in wider bridges and thicker connecting arms between the spheres. After curing of the wax-Styrofoam® expanded polystyrene sphere framing or body, the Styrofoam® expanded polystyrene spheres are removed. The following steps correspond to example 1, with suctioning into the cavities of the ceramic framing of the smaller Styrofoam® expanded polystyrene spheres, filling with ceramic material forming a ceramic mass, post-evacuating by cooling and subsequent dissolving of the shaping elements in acetone. Contrary to example 1, the cool drying step follows in steps of 2 hours each, in 70/80/90 and 3×100% acetone, cooling in air in steps in the freezer, at 4-12° C. increasingly in e.g. 4 steps of 3 hours each until room temperature is reached and subsequently dehydration in the vacuum and drying chamber by using $P_2O_5$ and a vacuum of about 150 mbar absolute pressure during 24 hours. Upon such a procedure, wide bridges between the porous spheres remain and the wax framing may be burnt at e.g. 1300° C. together with the ceramic inlet. The wax may also be melted off in the heat furnace at 90° C.; a precondition is that the ceramic mass is already dried in air. The result is a perfect framing made of interrelated, in the inside perfectly interconnected porous spheres with a continuous porous surface and an astonishingly high compression strength, which lies between 4-12 Mpa, depending on the size of the spheres.

Example (3)

This example relates to the production of a cube true in size, having an edge length of 15 mm and an open porosity over all surfaces. Upon a matrix mass of 16/35 HA/agar suspension of 1.7%, a shrinking factor of 1.91 is calculated and in a CAD/CAM process, a cube made of POM having an edge length of 28.65 mm is produced. Since the cube achieves a high strength of 4-6 Mpa, the edges are not rounded. The cube is put into a moulding tool and poured with self-curing silicone up to its top edge. After 24 hours, the cube is removed mechanically and the silicone tool is inserted into a filling tool, the bottom of which consists inside of a perforated silicone bottom and is covered in a flush manner with a silicone lid having venting holes after having been filled with 1200 μm sized Styrofoam® expanded polystyrene spheres. After the tool was closed with a screw cap having venting holes, it is filled with a ceramic material forming a ceramic mass. Subsequently, the charging with negative pressure of 500 mbar for 15 minutes upon simultaneous cooling occurs in the vacuum and drying chamber on a metallic and coolable setting plate. After that, the tool is de-assembled and the ceramic-Styrofoam® expanded polystyrene cube is carefully taken out mechanically and washed in acetone to remove the polystyrene spheres in the acetone washing, leaving a ceramic frame. For a crack-free drying, a cool dehydration follows, as described in examples 1 and 2, and subsequently, the ceramic frame cube is sintered in a furnace at about 1300° C. The result is a cube true in size and having a very high compressive strength, with open porosity over all surfaces and a continuously interconnecting porosity of the inner structure and reinforced edges made of solid ceramics.

The invention claimed is:

1. A porous implant body formed by application of a negative pressure resulting in said implant body comprising: an outer shell having a continuous surface the entirety of which is penetrated by pores having a predetermined diameter, and further including an inner structure defining a continuously interconnected cavity system made of hollow sphere-shaped cavities, wherein the implant body is configured such that each of the pores of the outer shell is directly connected to one of the cavities of the cavity system and each such connected pore has a diameter smaller than a maximum diameter of the directly connected cavity of the cavity system.

2. The porous implant body of claim 1, configured such that the outer shell is structured to include at least one of contractions and bulges.

3. The porous implant body of claim 1, configured such that the inner structure corresponds to a cancellous bone.

4. The porous implant body of claim 1, wherein the diameter of each of the pores of the outer shell is smaller than the maximum diameter of the directly connected cavity of the continuously interconnected cavity system in a ratio between 1:5 to 1:1.5.

5. The porous implant body of claim 1, having the shape of a porous sphere or a sphere-shaped structure of a size between 0.8 mm and 12 mm in diameter and the cavities of the interconnected cavity system having diameters of between 80 μm and 1500 μm.

6. The porous implant body of claim 1, wherein the inner structure and the outer shell are constructed from a group of materials consisting of a calcium phosphate, a hydroxyapatite, a calcium carbonate, a calcium-sulfate-composition, an aluminum oxide ceramic, a collagen, a polyaminoacid, an absorbable polymer, an acrylate or derivate thereof, a polymethyl-methacrylate, and a metal, the metal selected from the group consisting of a CoCrMo alloy, titanium, tantalum and alloys thereof.

7. The porous implant body of claim 1, configured such that the cavity system includes a filler material having dampening or reinforcing properties.

8. The porous implant body of claim 7, configured such that the filler material is selected from a group consisting of a poly-amino acid, a polylactide, polyglactine, glycoside, polyacetals, poly-acid amides and polyester.

9. The porous implant body of claim 7 wherein the filler material is selected from the group consisting of an absorbable inorganic material and an absorbable organic material.

10. The porous implant body of claim 1, configured such that at least some cavities are filled with a material, said material comprising an active agent which is released and diffuses over the surface of the outer shell.

11. The porous implant body of claim 1, configured such that said implant body includes at least one of an active agent, consisting of a growth factor, a bone morphogenetic protein or combination thereof.

12. The porous implant body of claim 1, configured such that the continuously interconnected cavity system includes wide and narrow cavities formed therein, and that the cavities are configured to accept filler materials and agents or combinations thereof.

13. The porous implant body of claim 1, wherein the surface of the outer shell has differing porosity, and wherein the inner structure includes at least one of a filler material and an active agent within the continuously interconnected cavity system.

14. The porous implant body of claim 1 and wherein the diameters of the pores of the outer shell are smaller than the maximum diameters of the respective cavities directly connected therewith in a ratio of between 1:3 and 1:2.

15. The porous implant body of claim 1, configured such that said implant body includes at least one of a hormone, an immunosuppressive drug, a cytostatic, and an antibiotic and combinations thereof.

16. The porous implant body of claim 1, configured such that said implant body includes an antibiotic.

17. The porous implant body of claim 16, wherein the antibiotic comprises one of Gentamycin, Clindamycin, Streptomycin and other bacteriostatic and bactericide agents.

18. A porous implant body having an outer shell having a continuous surface penetrated by pores having a predetermined diameter, and further including an inner structure comprising a conglomerate of cavities defined by sphere-shaped shells, said cavities forming a continuously interconnected cavity system made of hollow sphere-shaped cavities, wherein the implant body is configured such that each of the pores of the outer shell is directly connected to one of the cavities of the cavity system and each such connected pore has a diameter smaller than a maximum diameter of the directly connected cavity of the cavity system, manufactured by the process comprising:
providing a tool having an inner cavity;
placing shaping elements into the inner cavity of the tool;
adding a liquid mass to the inner cavity of the tool, wherein the liquid mass encompasses the shaping elements and defines the inner structure and the outer shell;
subjecting the inner cavity of the tool to a vacuum;
solidifying the mass by cooling;
removing the shaping elements; and
dehydrating, drying and sintering the mass.

19. A porous implant body formed by the application of a negative pressure resulting in said implant body comprising:
an outer shell having a surface the entirety of which is interrupted by pores across the entire surface, and further including an inner structure defining a continuously interconnected cavity system made of hollow sphere-shaped cavities, wherein the implant body is configured such that each of the pores of the outer shell is directly connected to one of the cavities of the cavity system and each such connected pore has a diameter smaller than a maximum diameter of the directly connected cavity of the cavity system.

20. A method of producing a porous implant body, the method comprising:
providing a tool having an inner cavity;
placing shaping elements into the inner cavity of the tool;
adding a liquid mass to the inner cavity of the tool, the liquid mass encompasses the shaping elements and defines an inner structure and an outer shell of the porous implant body;
subjecting the inner cavity of the tool to a vacuum;
solidifying the mass by cooling and thereby solidifying the inner structure and the outer shell of the porous implant body;
removing the shaping elements to create an outer shell having a continuous surface the entirety of which is penetrated by pores having a predetermined diameter, and further including an inner structure defining an interconnected conglomerate of sphere-shaped cavities within the inner structure and forming pores that interrupt the continuous surface of the outer shell wherein each of the pores in the outer shell is directly connected to one of the cavities of the cavity system and each such connected pore has a diameter smaller than a maximum diameter of the directly connected cavity of the cavity system;
dehydrating the outer shell and the inner structure;
drying the outer shell and the inner structure; and
sintering the outer shell and the inner structure.

21. The method of claim 20, and where providing the tool having an inner cavity comprises:
providing a tool having a deformable mold having the inner cavity.

22. The method of claim 20 and wherein placing shaping elements into the inner cavity of the tool comprises:
placing expandable polystyrene spheres into the inner cavity.

23. The method of claim 22 and wherein a size of the pores in the outer shell can be controlled by subjecting the expandable polystyrene spheres to a selected amount of vacuum which causes the spheres to expand to a desired volume and causes a portion of the sphere against a wall defining the inner cavity which defines the pore size in the outer surface.

24. The method of claim 20 and wherein adding a liquid mass to the inner cavity of the tool comprises:
adding a casting material comprising a solution comprising hydroxyapatite or a solution comprising a tricalcium-phosphate or combinations thereof.

25. The method of claim 20 and wherein subjecting the inner cavity of the tool to a vacuum comprises subjecting the inner cavity to a negative pressure of between 150 mbar and 800 mbar.

26. The method of claim 20 and wherein subjecting the inner cavity of the tool to a vacuum comprises subjecting the inner cavity to a negative pressure of between 300 mbar and 500 mbar.

27. The method of claim 20 and wherein solidifying the mass by cooling comprises cooling the mass to a temperature range between 4° C. and 12° C.

28. The method of claim 20 and wherein removing the shaping elements comprises:
subjecting the solidified mass to a washing in acetone.

29. The method of claim 20 and wherein dehydrating the outer shell and the inner structure comprises:
washing the outer shell and inner structure in a series of steps utilizing increasing concentrations of acetone.

30. The method of claim 20 wherein drying the outer shell and the inner structure comprises:
placing the outer shell and inner structure in a drying chamber; and
subjecting the drying chamber to a selected vacuum for a selected amount of time.

31. The method of claim 20 and wherein sintering the outer shell and the inner structure comprises:
placing the outer shell and the inner structure in a sintering oven at a temperature of around 1,300° C. for a selected amount of time.

* * * * *